(12) United States Patent
Gifford (10) Patent No.: US 11,573,432 B2
(45) Date of Patent: Feb. 7, 2023

(54) FITTING ORTHOKERATOLOGY LENSES

(71) Applicant: CAPRICORNIA CONTACT LENS PTY LTD, Queensland (AU)

(72) Inventor: Paul Gifford, Brisbane (AU)

(73) Assignee: CAPRICORNIA CONTACT LENS PTY LTD, Queensland (AU)

( * ) Notice: Subject to any disclaimer, the term of this patent is extended or adjusted under 35 U.S.C. 154(b) by 523 days.

(21) Appl. No.: 16/626,985

(22) PCT Filed: Jun. 28, 2018

(86) PCT No.: PCT/AU2018/050663
§ 371 (c)(1),
(2) Date: Dec. 27, 2019

(87) PCT Pub. No.: WO2019/000041
PCT Pub. Date: Jan. 3, 2019

(65) Prior Publication Data
US 2020/0133023 A1    Apr. 30, 2020

(30) Foreign Application Priority Data

Jun. 28, 2017 (AU) ............................... 2017902510

(51) Int. Cl.
*G06T 7/00* (2017.01)
*G02C 7/04* (2006.01)
(Continued)

(52) U.S. Cl.
CPC ............ *G02C 7/047* (2013.01); *A61B 3/0025* (2013.01); *A61B 3/107* (2013.01); *G06T 7/0014* (2013.01); *G06T 2207/30041* (2013.01)

(58) Field of Classification Search
CPC ....... G02C 7/047; A61B 3/0025; A61B 3/107; A61B 3/00; A61B 3/14; G06T 7/0014;
(Continued)

(56) References Cited

U.S. PATENT DOCUMENTS

| 5,592,246 A * | 1/1997 | Kuhn | G01B 11/255 351/212 |
| 5,867,250 A * | 2/1999 | Baron | A61B 3/107 351/212 |

(Continued)

FOREIGN PATENT DOCUMENTS

| CA | 2418654 C * | 4/2011 | ............. G02C 7/047 |
| EP | 2594192 A1 * | 5/2013 | ............ A61B 3/0025 |

(Continued)

OTHER PUBLICATIONS

International Search Report and Written Opinion from PCT Application No. PCT/AU2018/050663, dated Sep. 11, 2018.

*Primary Examiner* — Jose L Couso
(74) *Attorney, Agent, or Firm* — Workman Nydegger (57) ABSTRACT

A method for fitting OK lenses to a patient comprising the steps of: applying a corneal topography apparatus to a patient to capture baseline and post wear maps of a cornea of the patient in a computer to thereby derive a difference map; processing the difference map to fit Zernike polynomials thereto wherein weights of said fitted polynomials comprise features of a test feature vector for the difference map; applying the test feature vector to a classification machine trained to classify the difference map as one of a number of predetermined classes; and subsequently treating the patient taking into account the classification machine's classification.

19 Claims, 10 Drawing Sheets

(51) Int. Cl.
*A61B 3/00* (2006.01)
*A61B 3/107* (2006.01)

(58) Field of Classification Search
CPC . G06T 2207/30041; G06T 2207/20081; G06T 2207/20084; G06T 3/4046; G06T 9/002; G06T 7/75; G01B 11/2513; G01B 11/24; G16H 50/20; G06N 3/02; G06N 3/08–088; G06N 3/0454; G06N 7/00; G06N 20/00; G06K 7/1482; G06V 10/454; G06V 10/82; G06V 30/18057
See application file for complete search history.

(56) References Cited

U.S. PATENT DOCUMENTS

| | | | |
|---|---|---|---|
| 6,361,169 B1 | 3/2002 | Tung | |
| 7,025,460 B2* | 4/2006 | Smith | G02C 7/04 351/205 |
| 7,110,582 B1* | 9/2006 | Hay | A61B 3/12 382/128 |
| 8,366,272 B1* | 2/2013 | Myhill | G02C 7/024 351/212 |
| 8,888,286 B2* | 11/2014 | Grenon | A61B 3/101 351/221 |
| 9,339,177 B2* | 5/2016 | Grenon | A61B 3/0025 |
| 10,123,691 B1* | 11/2018 | Bagherinia | G06T 7/136 |
| 10,939,844 B2* | 3/2021 | Grundfest | A61B 5/4875 |
| 2005/0225724 A1* | 10/2005 | Klyce | A61B 3/107 351/200 |
| 2006/0152673 A1 | 7/2006 | Cotie et al. | |
| 2010/0061601 A1* | 3/2010 | Abramoff | G06V 40/197 382/117 |
| 2013/0044292 A1* | 2/2013 | Myhill | G02C 7/024 351/219 |

FOREIGN PATENT DOCUMENTS

| | | | | |
|---|---|---|---|---|
| JP | 2013-529946 A | * | 7/2013 | ............. A61B 3/107 |
| TW | 497970 B | * | 8/2002 | ............. G02C 7/047 |
| WO | 9109564 A1 | | 7/1991 | |
| WO | WO-2008014544 A1 | * | 2/2008 | ............. G02C 7/047 |
| WO | WO-2008131479 A1 | * | 11/2008 | ........... A61B 3/0025 |
| WO | WO-2011153256 A1 | * | 12/2011 | ........... A61B 3/0025 |
| WO | WO-2013081619 A1 | * | 6/2013 | ............. A61B 3/14 |
| WO | WO-2014148922 A2 | * | 9/2014 | ............. G02C 7/047 |

\* cited by examiner

FITTING ORTHOKERATOLOGY LENSES

TECHNICAL FIELD

The present invention relates to a method and apparatus for assisting a practitioner to identify corneal conditions such as keratoconus. The invention also relates to a method and apparatus for assisting a practitioner to therapeutically fit orthokeratology ("OK") lenses to a patient for alleviating conditions such as myopia, hyperopia, astigmatism and presbyopia.

BACKGROUND

Any references to methods, apparatus or documents of the prior art are not to be taken as constituting any evidence or admission that they formed, or form part of the common general knowledge.

Orthokeratology (OK) describes the use of specifically designed contact lenses that are typically worn overnight to temporarily correct refractive error. OK can be used to successfully correct myopia (short-sightedness), hyperopia (long-sightedness), astigmatism and presbyopia. During wear the OK lens moulds the anterior surface of the cornea and in doing so changes the refractive power of the eye.

OK contact lenses are fit by measuring the anterior curvature of the cornea, either using a keratometer or corneal topographer. While a keratometer provides basic corneal curvature information sufficient to choose an initial OK lens to fit a keratometer does not provide sufficient information to assess the change to corneal curvature that the lens induces during wear. For this reason, it is desirable to obtain a detailed analysis of corneal curvature shape using a corneal topographer.

Corneal topographers come in various permutations that can either be described as utilising reflective or scanning technology. Reflective topographers image the reflection of a known object that is illuminated on the cornea and analyse the captured image to build a 3-dimensional model, while a scanning topographer instead moves a light beam across the eye and records the change to the reflected pattern of the light beam as it is moved to build a 3-dimensional model. In all cases the 3-dimensional model is displayed as a 2-dimensional heat map that can be displayed on a computer screen. All computerised corneal topographers, regardless of type, provide a digital output of corneal shape descriptors including axial curvature, tangential curvature and sagittal height.

To measure change to corneal topography from OK lens wear a corneal topography image is captured before lens wear to form a baseline map and a second image is captured after lens wear to form a post wear map. The corneal curvature data describing the post wear map is then subtracted from the baseline map data to create a subtraction or difference map. The 2-dimensional heatmap of the difference map is then assessed by the OK practitioner to indicate how well the OK lens is fitting and to aid the practitioner's decision-making process on how to change the OK lens parameters if the fit needs to be altered.

A common convention is that where the cornea curvature has steepened relative to baseline the difference heat map is typically coloured red, conversely where the cornea has been flattened the heat map is typically coloured blue and is coloured green where there is no change.

The process the practitioner follows is to identify predefined shapes in the corneal topography difference heat maps as follows:

Bullseye: Central area of blue (corneal flattening) surrounded by a red annulus (corneal steepening).

Central Island: Similar in appearance to bullseye with central area of blue surrounded by a red annulus, except that the central blue area contains a small patch of red indicating centrally localised corneal steepening.

Smiley Face: Superior displaced area of blue surrounded by a superiorly displaced red annulus where the inferior aspect of the ring is more pronounced.

Frowney Face: Inferior displaced area of blue surrounded by an inferior displaced red annulus where the superior aspect of the ring is more pronounced.

Lateral Decentration: Laterally displaced area of blue surrounded by a laterally displaced red annulus where the opposite side of the red ring to the direction of lateral displacement is typically more pronounced.

By correctly classifying the difference map the practitioner is able to appreciate the change that the wearing of the OK lens has wrought and is thus able to treat the patient by either continuing with that lens or select a differently shaped lens in order to arrive at the desired corneal topography for the patient in question.

A difficulty that some practitioners face, particularly novice practitioners who have little or no experience in OK lens fitting, is that they may not find it straightforward to interpret the heat maps. The heat maps are not always readily classifiable and there may be situations where novice practitioners in particular may find it very challenging to interpret and correctly classify the heat maps. It will be realised that if the 2-dimensional heatmap of the difference map cannot be accurately interpreted then it cannot be used to aid the practitioner's decision-making process on how to change the OK lens parameters if the fit needs to be altered.

It is an object of the present invention to provide a method and apparatus for classifying corneal topography maps to assist a practitioner to provide therapy to a patient.

SUMMARY OF THE INVENTION

According to a first aspect of the present invention there is provided an apparatus for classifying corneal topography maps into one of a number of predetermined classes including:

an input unit for converting data from a corneal topography unit into a corneal map;

a feature extraction unit arranged to process the corneal map to fit Zernike polynomials thereto wherein weights of said fitted polynomials comprise features of a test feature vector;

a classification unit trained to classify test vectors for corneal maps and responsive to the feature extraction unit, wherein the classification unit is arranged to classify the test feature vector as corresponding to one of the number of predetermined classes; and an electronic display that is responsive to the classification unit for presenting classifications to a human user.

According to a further aspect of the present invention there is provided a method to therapeutically treat an eye condition related to the shape of the cornea, the method comprising the steps of:

applying a corneal topography apparatus to a patient to capture a map of a cornea of the patient in a computer;

processing the corneal map to fit Zernike polynomials thereto wherein weights of said fitted polynomials comprise features of the test feature vector;

applying the test feature vector to a classification machine trained to classify the difference map as one of a number of predetermined classes; and subsequently treating the patient taking into account the classification machine's classification.

According to another aspect of the present invention there is provided a method to therapeutically treat an eye condition related to the shape of the cornea, the method comprising the steps of:

applying a corneal topography apparatus to a patient to capture a map of a cornea of the patient in a computer;

extracting one or more feature vectors from the map including at least features identifying a red ring of the cornea;

applying the one or more feature vectors to a classification machine trained to classify the difference map as one of at least:
i "bullseye" OR "central island", and
ii "smiley face", and
iii "frowney face", and
iv "lateral decentration"; and subsequently treating the patient taking into account the classification machine's classification.

Preferably the step of extracting the features identifying the red ring of the cornea include determining central XY coordinates of a circle fitted to a red ring observed in the map.

Preferably the step of extracting the features identifying the red ring of the cornea further includes determining long and short axes of an ellipse fitted to the red ring.

Preferably the corneal topography map comprises a difference map, wherein the method includes the steps of:

applying the corneal topography apparatus to the patient to capture a baseline map of a cornea of the patient in the computer;

subsequent to the patient wearing an OK lens on the cornea applying the corneal topography apparatus to the patient to capture a post-wear map of the cornea in the computer;

and deriving the difference map from the baseline map and the post-wear map.

Preferably the step of subsequently treating the patient taking into account the classification machine's classification includes fitting an OK lens to the patient wherein said lens is selected based on the classification machine's classification of the difference map. It will be realized that a primary intended use of a preferred embodiment of the invention is to assist practitioners in altering the lens fit specifications of the initial fit lens that was worn between capture of the baseline and post wear topography maps.

Preferably the step of extracting one or more feature vectors from the difference map includes extracting curvature estimates of the difference map and applying the one or more features to a classification machine trained to classify the difference map as one of at least:
i) "bullseye", and
ii) "smiley face", and
iii) "frowney face", and
iv) "lateral decentration", and
v) "central island".

In preferred embodiment of the present invention the method includes extracting curvature estimates of the difference map by fitting Zernike polynomials to the difference map.

The method may include fitting Z4, Z7, Z8, Z12, Z17, Z18 and Z24 Zernike polynomials.

It is preferred that the method includes obtaining features corresponding to 14 Zernike components from axial curvature difference map data measured over a 3.5 mm pupil, Preferably the method also includes obtaining features corresponding to 14 Zernike components from axial curvature and tangential curvature difference maps data measured over a 5.5 mm pupil.

The classification machine preferably includes one of: a Decision Forest; Decision Jungle; Logistic Regression Machine; Neural Network; Support Vector Machine.

According to a further aspect of the present invention there is provided an apparatus for classifying corneal topography maps into one of a number of predetermined classes including:

an input unit arranged to convert data generated by a corneal topographer into a corneal map;

a feature extraction unit arranged responsive to the input unit and arranged to process the corneal map to produce a corresponding test feature vector, wherein the feature extraction unit is arranged to identify a red ring of the map and to fit one or more shapes to the red ring wherein parameters of said shapes comprise features of the feature vector;

a classification unit trained to classify test vectors for corneal maps and responsive to the feature extraction unit, wherein the classification unit is arranged to classify the test feature vector as one of at least:
i) "bullseye" OR "central island", and
ii) "smiley face", and
iii) "frowney face", and
iv) "lateral decentration"; and an electronic display that is responsive to the classification unit for presenting classifications to a human user.

Preferably the feature extraction unit is arranged to fit shapes comprising a circle and an ellipse to the red ring.

In a preferred embodiment of the invention the feature extraction unit is further arranged to process the corneal map to fit Zernike polynomials thereto wherein weights of said fitted polynomials comprise further features of the test feature vector and wherein the classification unit is trained to classify test vectors including said weights to classify the test feature vector as one of at least:
i) "bullseye", and
ii) "smiley face", and
iii) "frowney face", and
iv) "lateral decentration", and
v) "central island".

According to a further aspect of the present invention there is provided a method for fitting OK lenses to a patient comprising the steps of:

applying a corneal topography apparatus to a patient to capture baseline and post wear maps of a cornea of the patient in a computer to thereby derive a difference map;

processing the difference map to fit Zernike polynomials thereto wherein weights of said fitted polynomials comprise features of a test feature vector for the difference map;

applying the test feature vector to a classification machine trained to classify the difference map as one of a number of predetermined classes; and subsequently treating the patient taking into account the classification machine's classification.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

Figure 1:
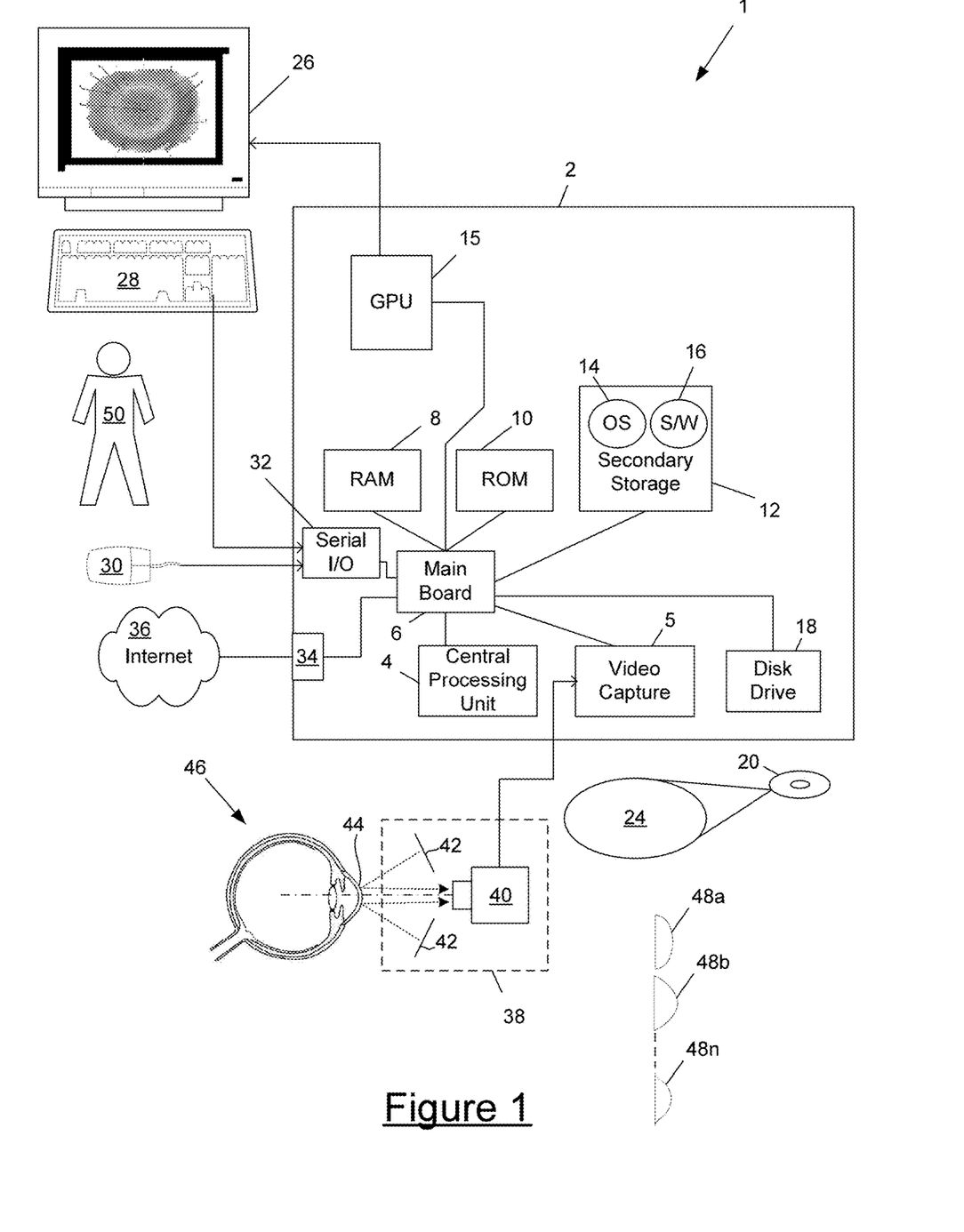
FIG. 1 depicts an apparatus 2 according to a first embodiment of the present invention, shown in use.

FIG. 1 depicts an apparatus 1 according to a first embodiment of the present invention, shown in use. The apparatus comprises a specially programmed computer 2 which is coupled to a corneal topography apparatus 38. The computer 2 includes a central processing unit (CPU) 4 which is comprised of one or more microprocessors which may have one or more core processing units. The CPU 4 communicates with peripheral units via a main board 6 which is formed with various data communication busses and which provides power to the CPU 4 and other components of the computer 2. In particular, the main board 6 communicates with a read only memory (ROM) 10 which stores BIOS instructions for boot up of the computer. Upon boot up the CPU 4 loads instructions from operating system (OS) 14, stored in secondary storage 12 (e.g. a hard disk or solid state disk), into random access memory (RAM) 8 and executes those instructions to implement the OS 14. The CPU 14 is responsive to commands entered by a human practitioner 50 by means of mouse 30, and keyboard 28 via serial input/output (I/O) controller 32 and is able to generate displays for presenting information and prompting for input on display screen 26 via graphical processing unit (GPU) 15. The CPU 4 is also responsive to data from the corneal topography unit 38 which is interfaced to the CPU 4 via a video capture card 5. The corneal topography unit 38 includes a CCD imaging device 40 which converts light from light sources 42 reflected from an anterior surface of a patient's cornea 44 of the patient's eye 46. Corneal topography units are known in the prior art. The raw corneal topography data that is generated by the corneal topography unit includes axial curvature, tangential curvature and height in cartesian (X,Y, Z) format or polar (theta, rho, Z) format at points over the cornea 44.

In use the CPU 4 executes instructions of the software product 16 which as will be explained cause the CPU 4 to implement a classification procedure to assist practitioner 50 to select between various OK lenses 48a, . . . , 48n for shaping the cornea according to a method of the present invention. The software product 16 may be loaded from an installation program 24 which comprises non-transitory, tangible machine readable instructions borne on an optical or magnetic medium 20 for reading by a disk drive 18.

The Inventor has found that using the previously mentioned raw corneal topography data produces an extremely large array of features, which would result in in poor classification accuracy by a classification machine. While in a less preferred embodiment of the invention it is possible to use this entire data set of features, once sufficient examples have been captured, the training process for such a large feature set requires a very large number of training examples to achieve a useable degree of accuracy. A preferred embodiment of the invention, which will be described allows good classification accuracy to be achieved with a smaller number of training examples so that a classification machine can be more quickly put to effective use.

Figure 2:
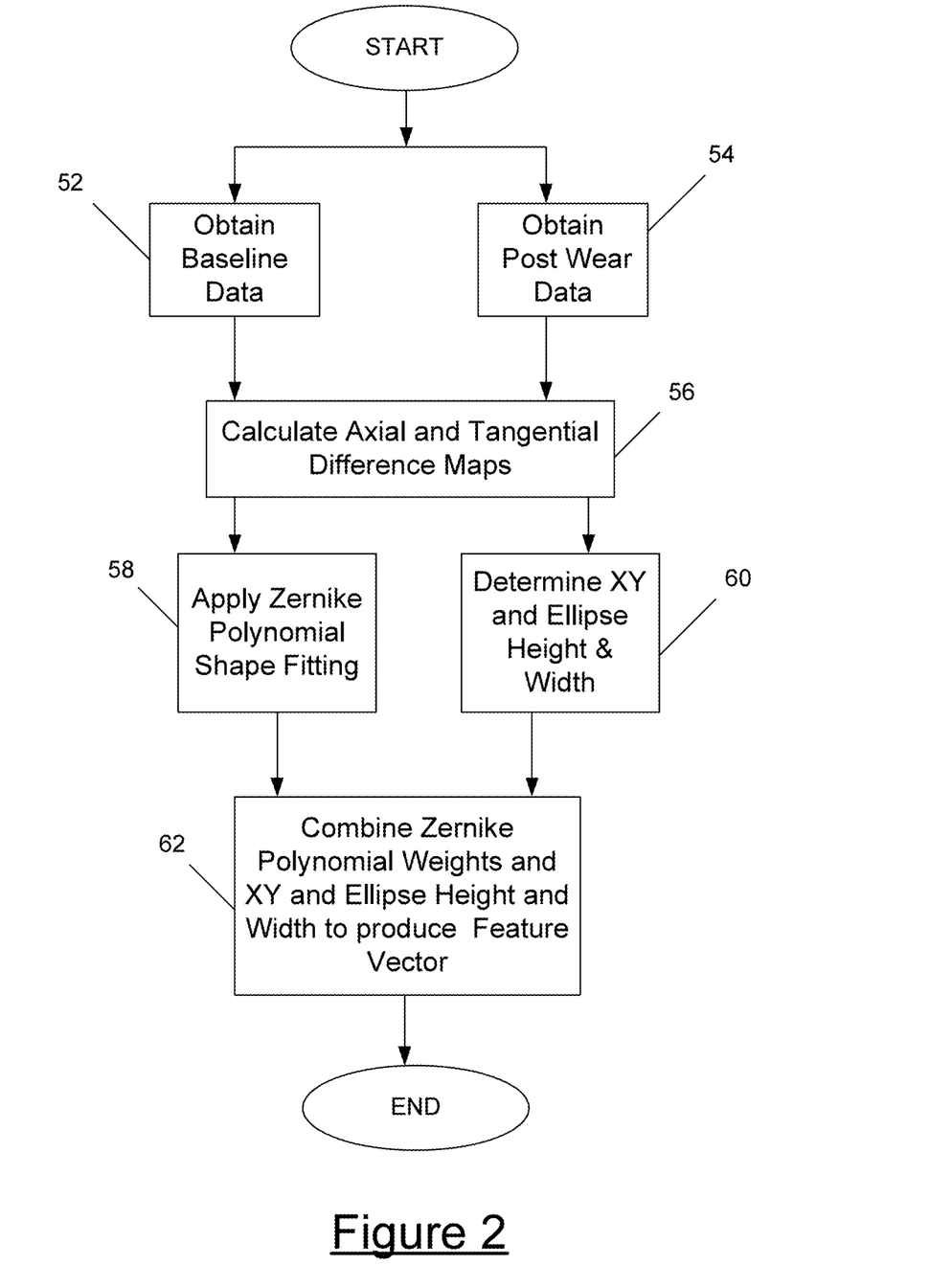
FIG. 2 is a high level flowchart of a method for generating feature vectors for a corneal topography difference map according to a preferred embodiment of the present invention.

FIG. 2 is a high-level flowchart of a preferred method that CPU 4 implements under control of instructions of the software 16 in order to determine feature vectors for the cornea according to a preferred embodiment of the present invention.

At boxes 52 and 54 data defining a patient's baseline and post wear corneal topography maps is retrieved. This data will typically comprise raw data from the corneal topography unit 38 which has been captured before and after wearing of one of the OK lenses 48a, . . . , 48n, by means of corneal topography unit 38. At box 56 the data that has been obtained is processed to calculate axial difference maps data and tangential difference maps data. Such processing is well known in the field of corneal topography.

Figure 3:
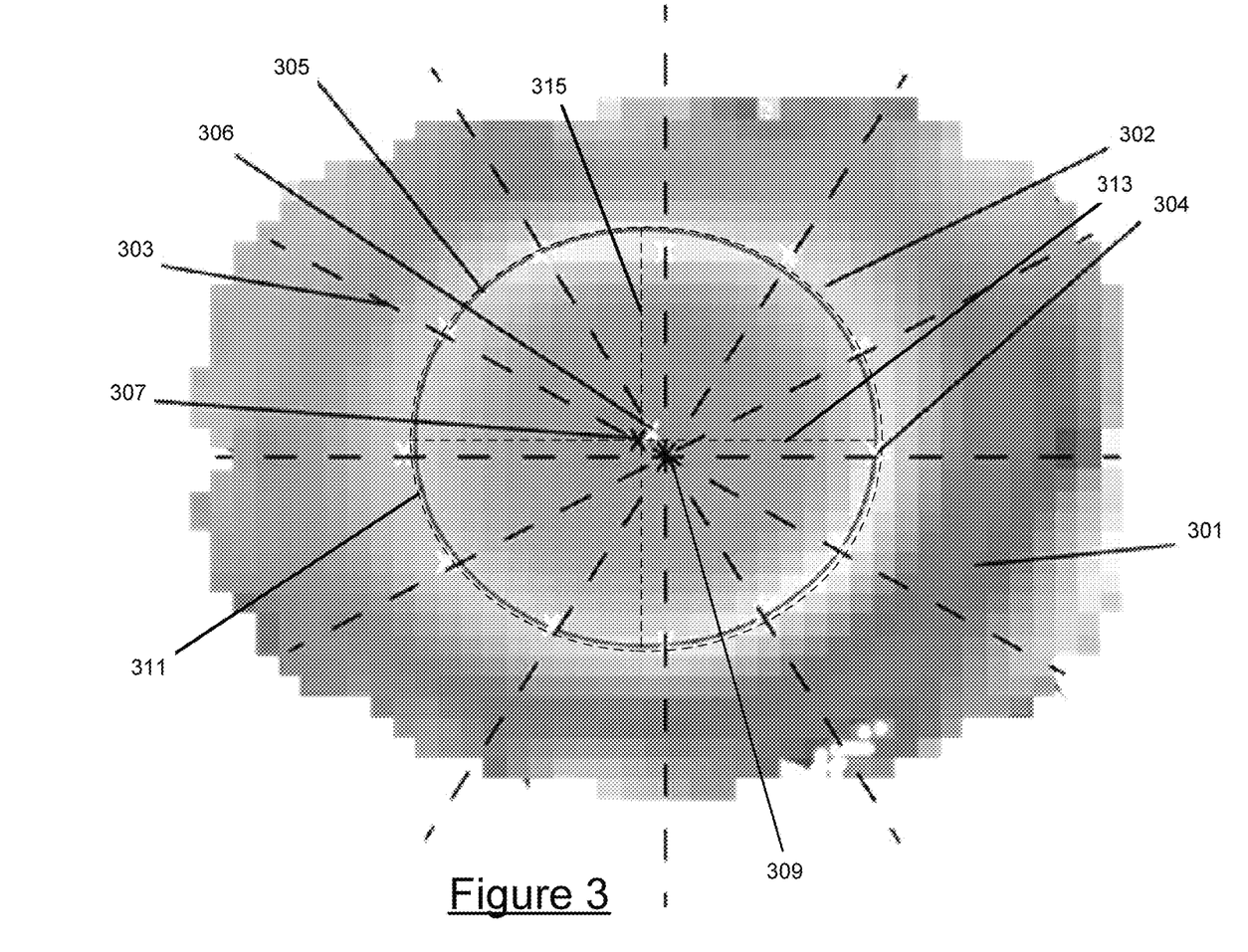
FIG. 3 illustrates the identification of the location of a red ring in a post orthokeratology (OK) wear tangential curvature corneal topography difference map.

The Inventor has also found that the relative position of the red ring, i.e. corneal steepening, identified as item 304 of FIG. 3 that is evident in tangential curvature maps post OK lens wear (FIG. 4) and described earlier, to the centre of the map is a good indicator of map type. Specifically, the XY centre coordinates (item 306 of FIG. 3) of a circle 5 fitted to the red ring, if close to the centre of the map is likely to indicate a bullseye, if superior to the centre of the map is likely to indicate a smiley face, if inferior to the centre of the map is likely to indicate a frowney face, and if lateral to the centre of the map is likely to indicate a lateral decentration. While this is one of the visual features that practitioners are able to observe when fitting OK lenses, it has to the best of the Inventor's knowledge, hitherto not been possible to automatically identify the valuable XY centre coordinates relative to the map centre of this feature.

Figure 5:
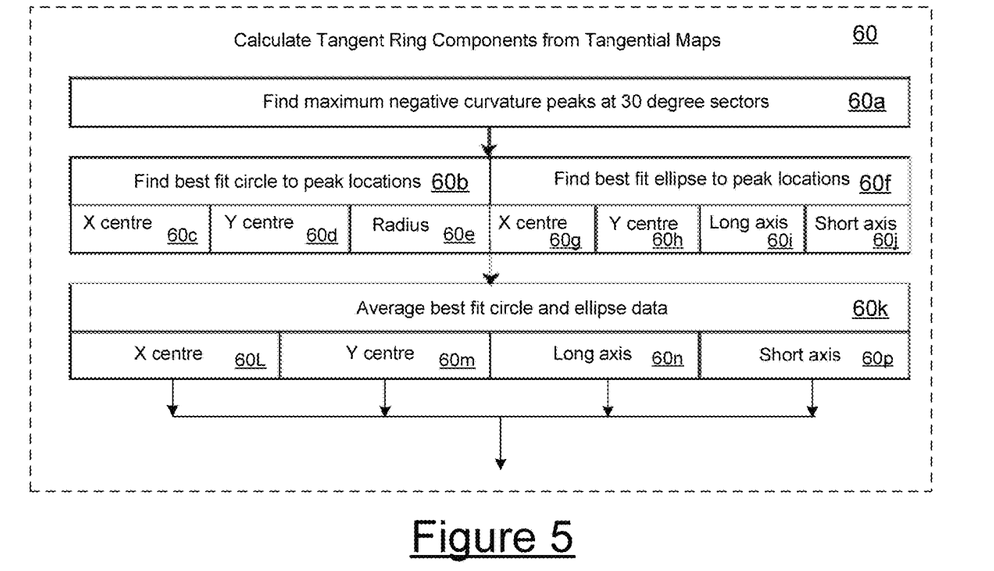
FIG. 5 is a detail of a box of the flowchart of FIG. 2 involving the identification and characterization of a "red ring" of the corneal topography difference map.

The method carried out in box 60 of FIG. 2, and shown in detail in FIG. 5, to calculate the values of these features involves interpolating the original tangential radius data, imported from the measured corneal topography tangential curvature difference map (illustrated as item 301 of FIG. 3), onto polar coordinates.

While other embodiments are possible, the Inventor has found 30 degree sectors and 0.1 mm steps along each radial spoke (item 303 of FIG. 3) to be effective. Data along each spoke 303 (depicted as the curve 401 of FIG. 4) is then analysed to detect the negative peaks where each data point immediately adjacent to either side of a given point of absolute value have a lower absolute value (e.g. item 402 of FIG. 4). At box 60*a* of FIG. 5, the depth of each peak is measured as the distance (item 404 of FIG. 4) to the first peak of opposite orientation either side of the peak (item 403 of FIG. 4). The width of each peak is then calculated along the X vector (perpendicular to the peak) as the distance between both sides of the peak (item 405 of FIG. 4). The height of each peak is then multiplied by the width of each peak, and the peak with the greatest height-by-width ratio is then identified as most likely to indicate the section of the tangential red ring in question. The radial position of the peak is then recorded by CPU 4 in secondary data storage 12 for later retrieval. This process is then repeated for each spoke in turn to return an array of radial values.

Figure 4:
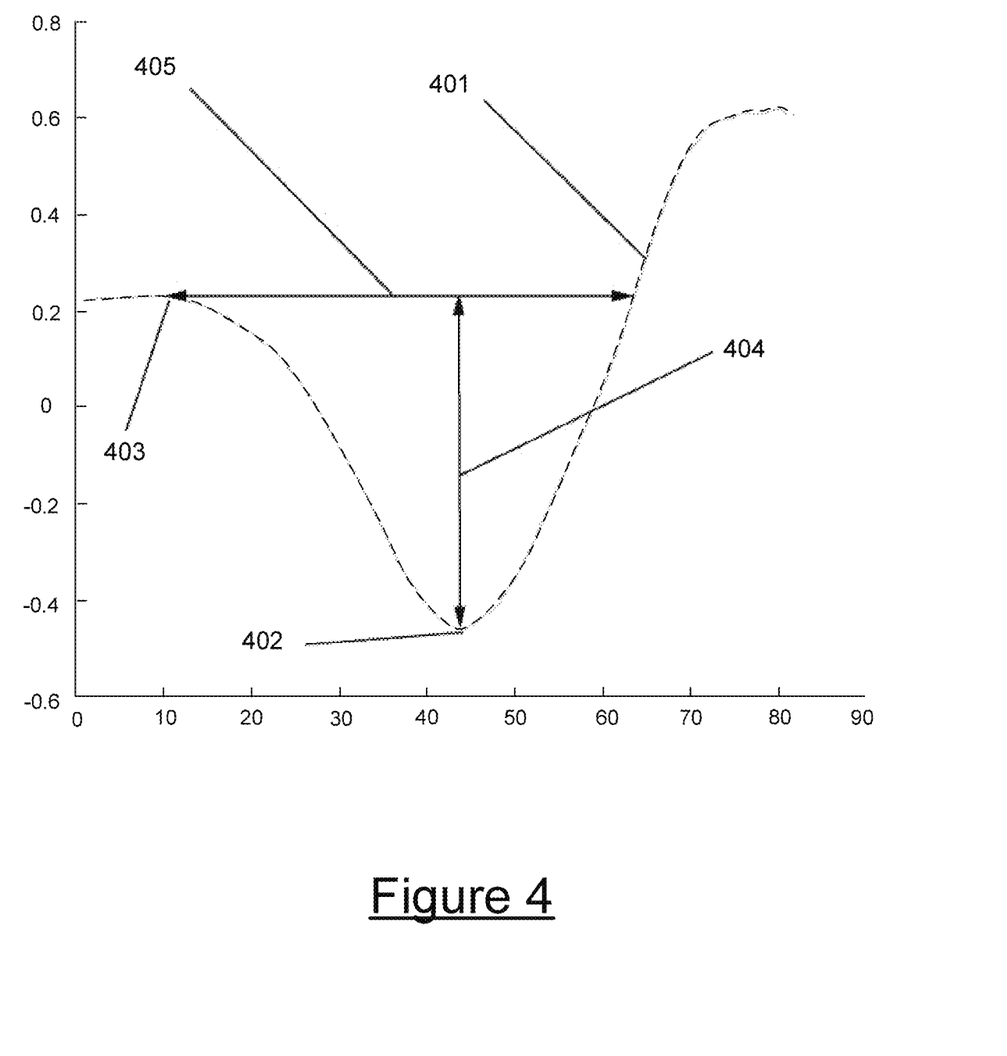
FIG. 4 is a diagram illustrating the maximum negative peak along a given radial section from the post orthokeratology wear tangential curvature corneal topography difference map of FIG. 3.

To check for potential outliers the software 16 includes instructions for the CPU to check for mean and standard deviation of the radial location dataset is calculated. Individual values that fall outside of the range mean minus a factor (e.g. 1.5) times the standard deviation to mean plus a factor (e.g. 1.5) times the standard deviation are excluded from further analysis. The remaining data points are then, at box 6*b* of FIG. 5, fit to a best fit with a circle (item 305 of FIG. 3) such that the circle radius and centre position relative to the centre of the map is optimised to provide the best least squares fit of the circle circumference to the maximum negative peak data points (item 304 of FIG. 3) established in the cross section analysis that is illustrated in FIG. 4. The X centre, Y centre and Radius values of the fitted circle are then stored at boxes 60*c*, 60*d* and 60*e*.

The fitting process is then repeated at box 6*f* but instead of fitting a circle, the fitting process at box 6*f* involves fitting a 2-dimensional ellipse to the data. Fitting the ellipse establishes the XY coordinates (item 307, FIG. 3) of the fitted ellipse relative to the centre of the map. The XY locations of the centres of the circle and of the ellipse and also the ellipse's long and short axes are then stored at boxes 60*g*-60*j*. At box 60*k* the XY circle centre and the XY ellipse centre are then averaged to provide a single X and Y coordinate that can be used to denote the XY centre of the tangential red ring stored at boxes 60L, 60*m*. The long and short axis lengths of the fitted ellipse are also retained at boxes 60*n*, 60*p* as an indicator of the red ring dimensions. Consequently, the important features of the tangential difference map red ring can be reduced from a typical array of 50×50=2500 individual data points to 4 values (X, Y, ellipse long axis length, ellipse short axis length). This process is repeated for each corneal topography difference map that is either being assessed for training or validating a machine learning model, or to be entered into the machine learning model for it to provide automated classification.

In the experimental process, it was realised that higher classification accuracy on validations sets is achieved if the fit circle X coordinate is converted to its absolute value as for classification purposes the direction of lateral displacement is irrelevant. However, this realisation does not discount that high accuracy can be established from using the circle fit or ellipse fit data in isolation.

The XY classification and fit ellipse dimensions alone are unable to detect the difference between a bullseye and central island To establish a reduced set of features that retained sufficient reliability for accurate machine learning classification, including discriminating between a bullseye and a central island, 1000 corneal topography difference maps from eyes fitted with OK lenses were analysed by the Inventor who is an OK lens fitting expert and categorised as being either Bullseye, Central Island, Smiley Face, Frowney Face or Lateral Decentration.

Using this dataset the Inventor discovered that the number of features can be considerably reduced to a small set of influential features by utilizing Zernike polynomial shape fitting to the corneal axial curvature and tangential curvature difference map data.

Figure 6:
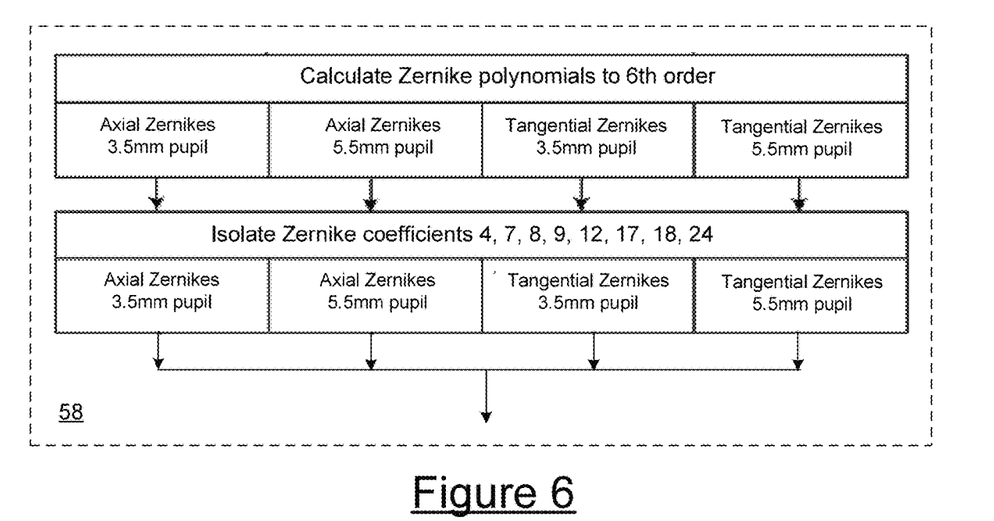
FIG. 6 is a detail of a box of the flowchart of FIG. 2 involving the fitting of Zernike polynomials to the corneal topography difference map.

With reference to FIG. 2, at box 58 a Zernike polynomial shape fitting procedure is applied to the axial and tangential difference maps data. FIG. 6 shows box 58 in a higher level of detail.

Zernike polynomials, their mathematical construct and methods to fit them to corneal shape data have been described extensively in the literature.

Zernike polynomials are a series of rotational mathematical constructs that can be used to describe different component shapes of a curved surface like the cornea. The weight of each individual Zernike polynomial that exists in a given surface can be easily calculated, resulting in a single number for each fitted Zernike polynomial. Zernike polynomials are additive allowing accurate reproduction of the fitted surface by returning the fitted values into each polynomial and summing the reconstructed shapes. Zernike polynomials can thus reduce the 2500 individual data points in a typical corneal topography map. The Inventor has found that the first 28 Zernike polynomials give sufficient data to retain the raw corneal topography map's appearance to a trained observer when the fitted Zernike polynomial coefficients are rebuilt. Thus 2500 data points can be reduced in the order of 100 times.

The Inventor has found that the most influential Zernike polynomial functions for corneal topography identification are those calculated over 3.5 mm and 5.5 mm pupils from axial curvature, tangential curvature and corneal height data. Furthermore, while various embodiments of the present invention may make use of Zernike polynomials up to any order and over any pupil diameter, for machine learning, the most influential to allow training with a small dataset are Z4, Z7, Z8, Z12, Z17, Z18, and Z24.

Figure 7:
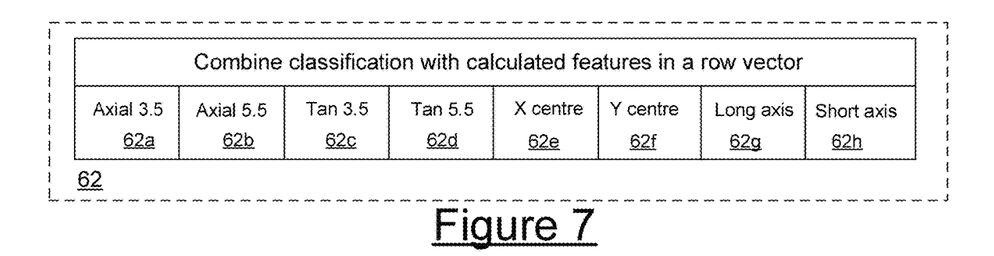
FIG. 7 is a detail of a box of the flowchart of FIG. 2 regarding the combination of extracted features to form a feature (row) vector.

Referring again to FIG. 2, at box 62 the Zernike polynomial weights and XY and ellipse long axis and short axis are combined to produce a feature vector that characterises the difference map that has been analysed. FIG. 7 illustrates the storing of the Z4, Z7, Z8, Z12, Z17 and Z24 Zernike polynomial weights for each of axial 3.5 mm and 5.5 mm and tangential 3.5 mm and 5.5 mm pupils at boxes 62*a*, . . . , 62*h*.

Figure 8:
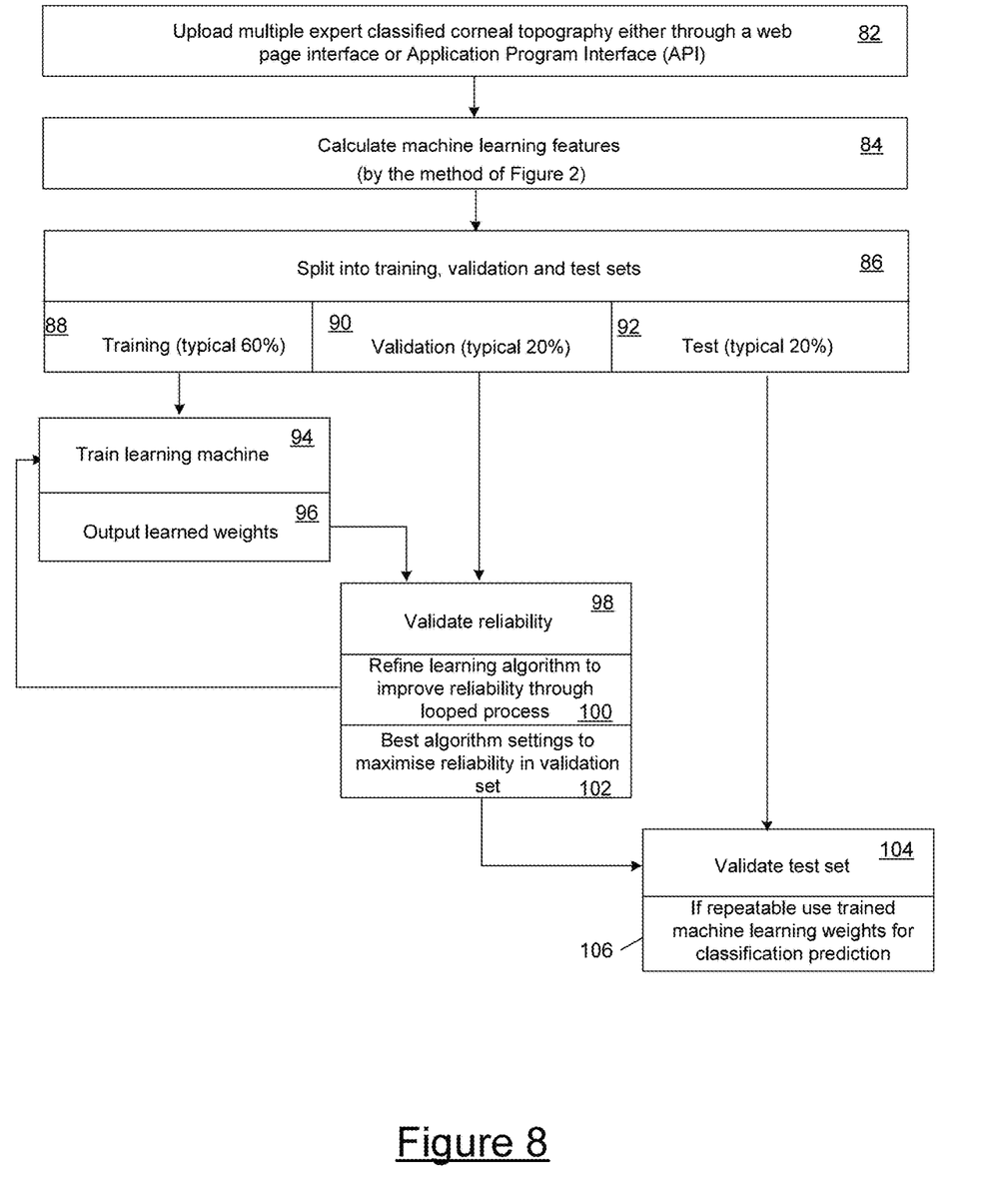
FIG. 8 is a flowchart of a procedure for training a classification machine according to a preferred embodiment of the present invention.

FIG. 8 is a block diagram of a procedure for training a classification machine to classify corneal topography maps.

Initially axial and tangential curvature difference maps are given to a trained OK lens fitting expert to classify them as either representing a Bullseye, Smiley Face, Central Island, Frowney Face or Lateral Decentration pattern. The expert classification along with the corresponding map data are uploaded at box 82.

The previously described steps to fit Zernike polynomials to the axial and tangential curvature difference maps and calculate the XY centre coordinates of the red ring present in the tangential difference maps to each of the axial curvature corneal topography difference maps that form the training data are carried out for each of the classified maps at step 84.

These data, which are typically called the X values when used in machine learning algorithms, are then converted into a table where columns represent the Zernike coefficient and XY features, and each row represents a training example. Thus the table will have 32 columns and m number of rows where m is the number of training examples and the 32 columns comprise the 28 Zernike polynomial terms and the 4 terms representing the XY position and dimensions of the red ring present in the tangential difference map.

At box 86, to ensure that an accurate training end point has been achieved, and the data not over fitted by the machine learning process these data are further separated into validation and test sets in the ratio 60:20:20 (training: validation: testing), boxes 88, 90, 92. It will be realised that other training validation and testing set ratios may be used as are known in the art of machine learning. The classification values for each training/validation/testing example, typically given the label Y, are recorded in a column value of m length, where each value matches the corresponding row of the X value table.

These data are then used (boxes 94, 96) to train a classification machine wherein an iterative process is used to establish the weights (theta values) to apply to the X values towards achieving a classification that aligns the Y values (FIG. 1). The validation set 90 is used to assist this process to indicate the optimum values for the additional machine learning variables that are used to fine tune the fit accuracy of the algorithm (boxes 98-102). The conducted experimental process has revealed that a Multiclass Decision Forest algorithm provided the highest accuracy followed by similar though slightly reduced accuracy from a neural network or support vector machine, and still good, but less accuracy still from a logistic regression algorithm.

Approximately 95% fit accuracy was found on the training set (box 104) and approximately 85% fit accuracy on the validation set and testing set was found from the refined corneal topography data in these machine learning models. Higher accuracy can be achieved in the training set but this is at the cost of over fitting the data leading to reduction in accuracy when applied to the validation and test sets. This however indicates that higher accuracy can be achieved in all sets through increasing the number of examples that are included in the training set.

Figure 9:
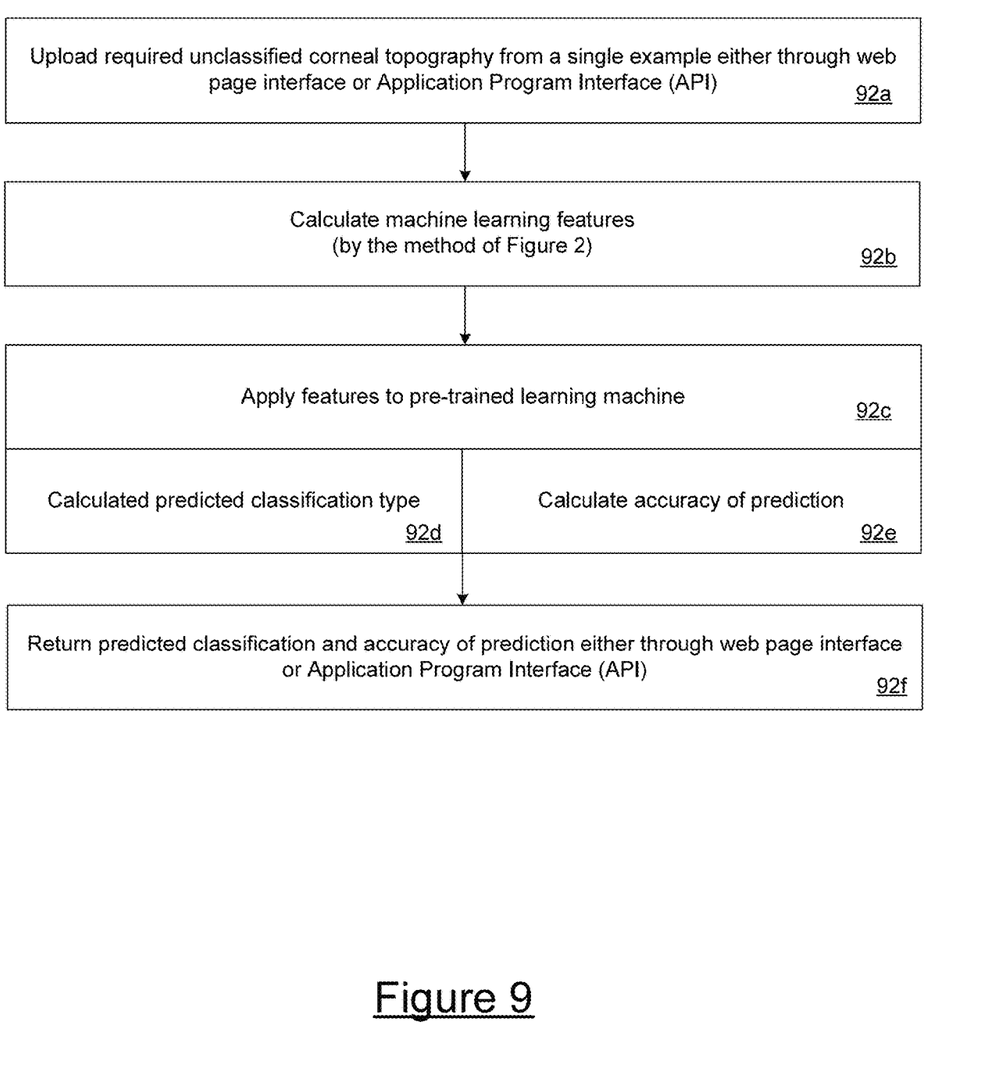
FIG. 9 is a flowchart of a procedure for classifying test feature vectors extracted from corneal topography difference maps according to a preferred embodiment of the present invention.

With reference to the flowchart of FIG. 9, after running the training process, the trained theta values, i.e. the weights arrived at in box 106, can then be applied to classify new presentations of corneal topography difference maps. This is done by repeating the identical processes used on the training and validation sets of automatically finding the centre coordinates of the red ring present in the tangential difference map alongside the ellipse and circle fit data and axial and tangential curvature Zernike fits for Z4, Z7, Z8, Z12, Z17, Z18, and Z24 at 3.5 mm and 5.5 mm pupils (box 92*b*).

This reduced dataset is then passed to the trained classification machine (box 92*c*) to return a classification (box 92*d*) that can be implemented in any suitable software package used for OK lens fitting, thus aiding the practitioner 50 (FIG. 1) to identify how well the OK lens represented by the captured topography maps is fitting. An accuracy value of the prediction may also be calculated and returned (box 92*e*).

The calculated predicted classification type (box 92*f*) and accuracy value are then returned for display Over time sufficient accumulation of corneal topography difference map data arises to improve the accuracy of the classification machines through retraining. In applying the processes described above at least 80% confidence may be given in automated classification of any post orthokeratology wear corneal that are fed into classification machine that has been trained to identify the features described above. To improve accuracy any incorrect classification given by the learning algorithm, as identified by an expert in the art of fitting orthokeratology contact lenses, is relabelled and collected alongside correctly classified maps.

Periodically as the collection of map data increases the collected maps can be randomly added to the original training, validation and testing sets while maintaining their relative 60/20/20 ratio, and the learning algorithm retrained using the larger training set. The Inventor's evidence of experimental process suggests that increasing the size of the training set will lead to improved accuracy of the learning algorithms ability to correctly detect the map type of newly introduced maps.

As the training set size increases it is recognised that the number of image identifying features required to achieve accurate identification could be reduced. For example it may be that the number of fitted Zernike components could be reduced or the dimensions of the red ring may not be required. This would have the effect of reducing the computing power required to train a machine learning algorithm and simplify the corneal topography data preparation process. However, the high classification accuracy that has been established using the algorithms described within this application demonstrate that including the Zernike fit and red ring fit features that have been described are likely to give greater classification machine classification accuracy.

Figure 10:
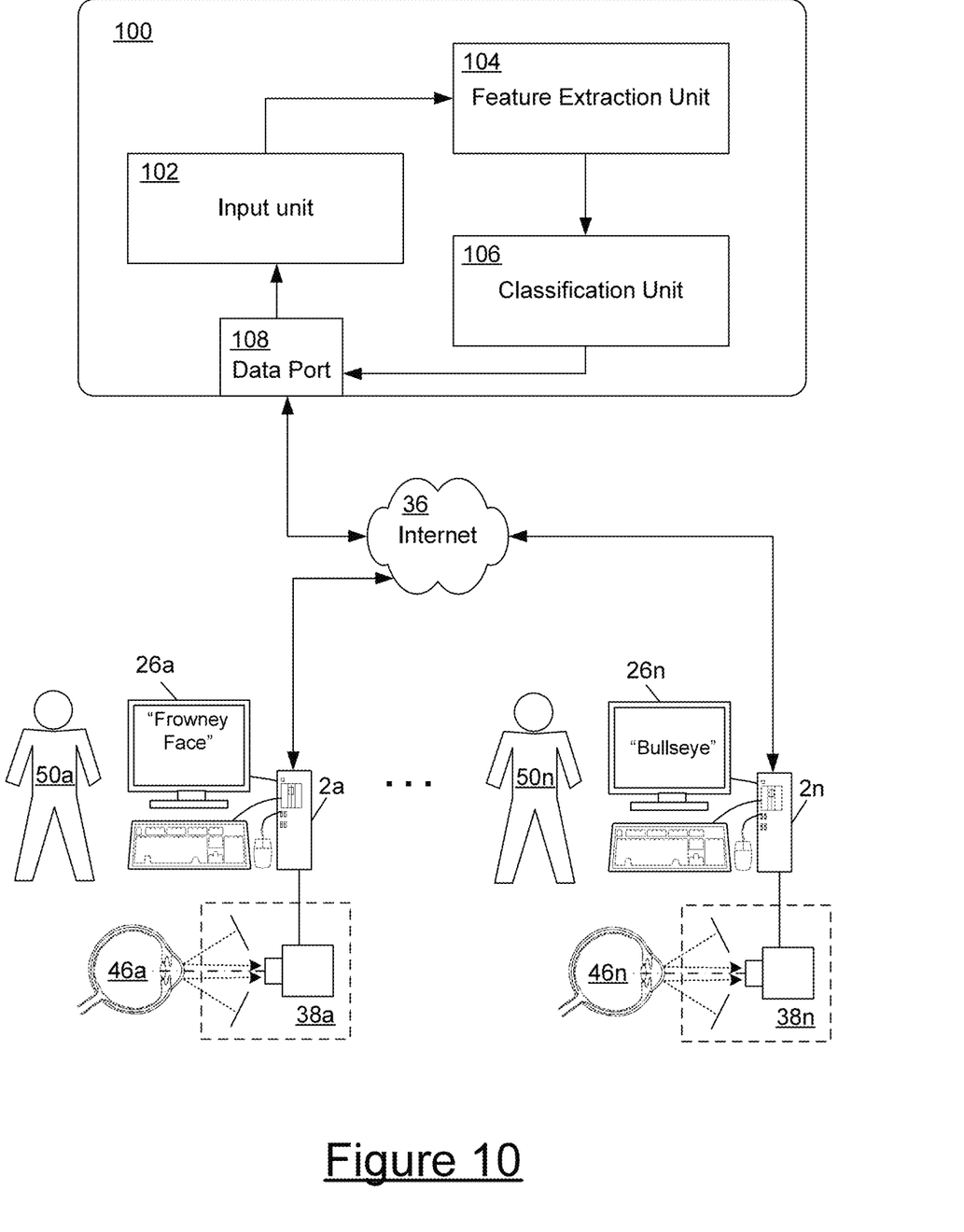
FIG. 10 is a flowchart of a general procedure for analyzing corneal topography maps using Zernike polynomial analysis to form feature vectors for training a classification machine and using the trained classification machine for classifying test feature vectors.

FIG. 10 illustrates an apparatus 100 in the form of a specially programmed server that is configured to classify corneal topography data of patient's eyes 46*a*, . . . , 46*n* that are captured by corneal topography units 38*a*, . . . , 38*n* and submitted from remote computers 2*a*, . . . , 2*n* via internet 36.

The apparatus 100 is arranged to classify corneas has having one of number of predetermined shapes. Apparatus 100 includes an input unit 102 that is arranged to convert data from corneal topography units 38*a*, . . . , 28*n* into corneal maps. Output from the Input Unit 102 is coupled to a feature extraction unit 104 that is arranged to process corneal maps to produce a corresponding test feature vector. The feature extraction unit 104 is arranged to identify a red ring of the map in the manner that has previously been described and to fit one or more shapes, such as a circle and an ellipse, to the red ring. As previously discussed, parameters of the shapes such as their center and ellipse height and width are used as features of the feature vector.

A classification unit 106 is coupled to the output side of the feature extraction unit 104 and receives test feature vectors from the feature extraction unit. The classification unit 106 is trained to classify the test vectors for the corneal maps. Where the feature extraction unit makes use of the red ring circle and ellipse fitting parameters, the classification unit is arranged to classify the test feature vector as one of at least:
I. "bullseye" OR "central island", and
II. "smiley face", and
III. "frowney face", and
IV. "lateral decentration";

In the preferred embodiment of the invention the feature extraction unit 104 also calculates Zernike polynomial weight features so that those features also form part of the test feature vector. In that case the classification unit is trained to take the Zernike polynomial features of the test feature vector into account so that it may also discriminate between bullseye and central island shapes.

The classification that is determined by the classification unit 106 is then returned to the corresponding remote computer 2a, ..., 2n via data port 108 and internet 36 so that an electronic display 26a, ..., 26n that is responsive to the classification unit 106 is able to present the classification to a human user such as practitioners 50a, ..., 50n.

The server 100 may be that implement by means of a cloud based solution. Examples of suitable cloud based platforms, without limitation, include Microsoft Azure or Amazon AWS. In this way a system is provided wherein practitioners 50a, ..., 50n can easily upload the raw, before (baseline) and, after OK wear corneal topography maps for the pre-trained classification unit 106 to return a classification and probability score describing the accuracy of the classification.

Figure 11:
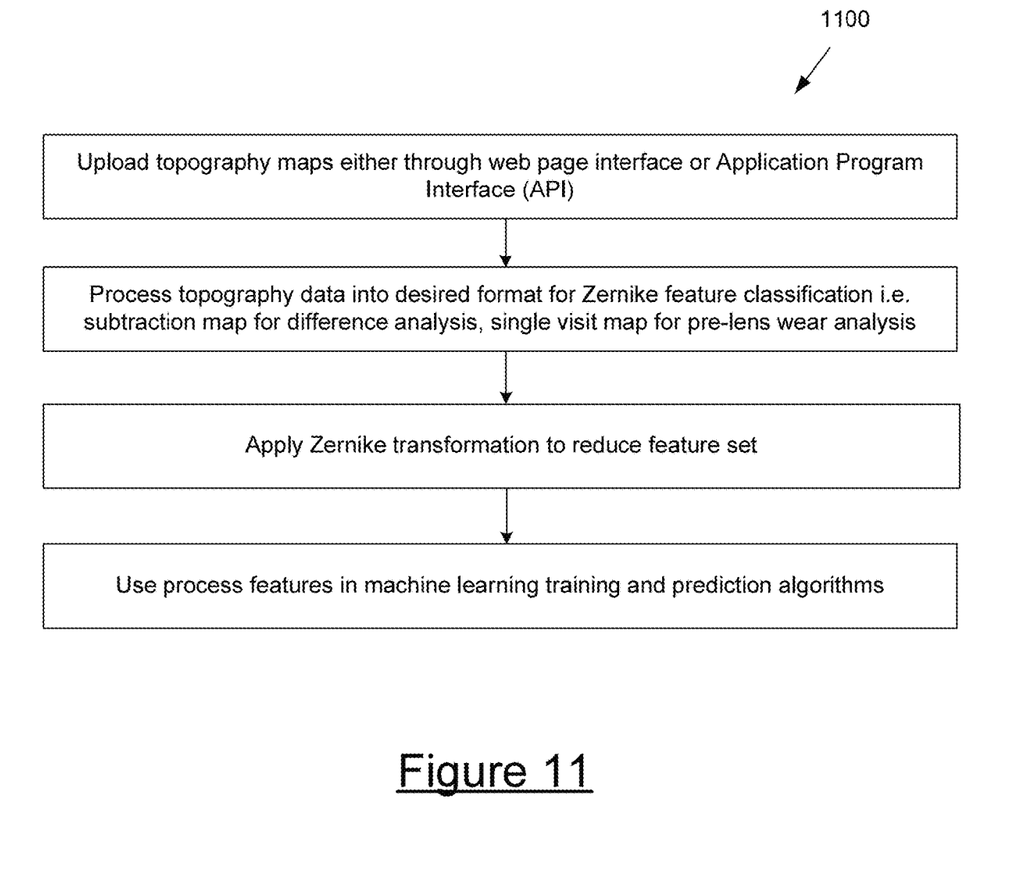
FIG. 11 is a flowchart of a method according to a further embodiment of the present invention.

Although the feature extraction steps described herein have been discussed in the context of analysis of corneal topography maps obtained from orthokeratology contact lens wear, they can similarly be applied to other types of corneal topography analysis. FIG. 11, presents a flowchart 1100 of a method according to a further embodiment of the present invention such as but not limited to the categorization of the best type of contact lens to fit to a given eye or to identify corneal health conditions such as keratoconus. For example, a corneal map may be classified as indicative or non-indicative of the presence of keratoconus. Where a corneal condition, such as keratoconus is indicated by the classifier then the health practitioner may take steps to apply a suitable therapy to the patient.

Figure 12:
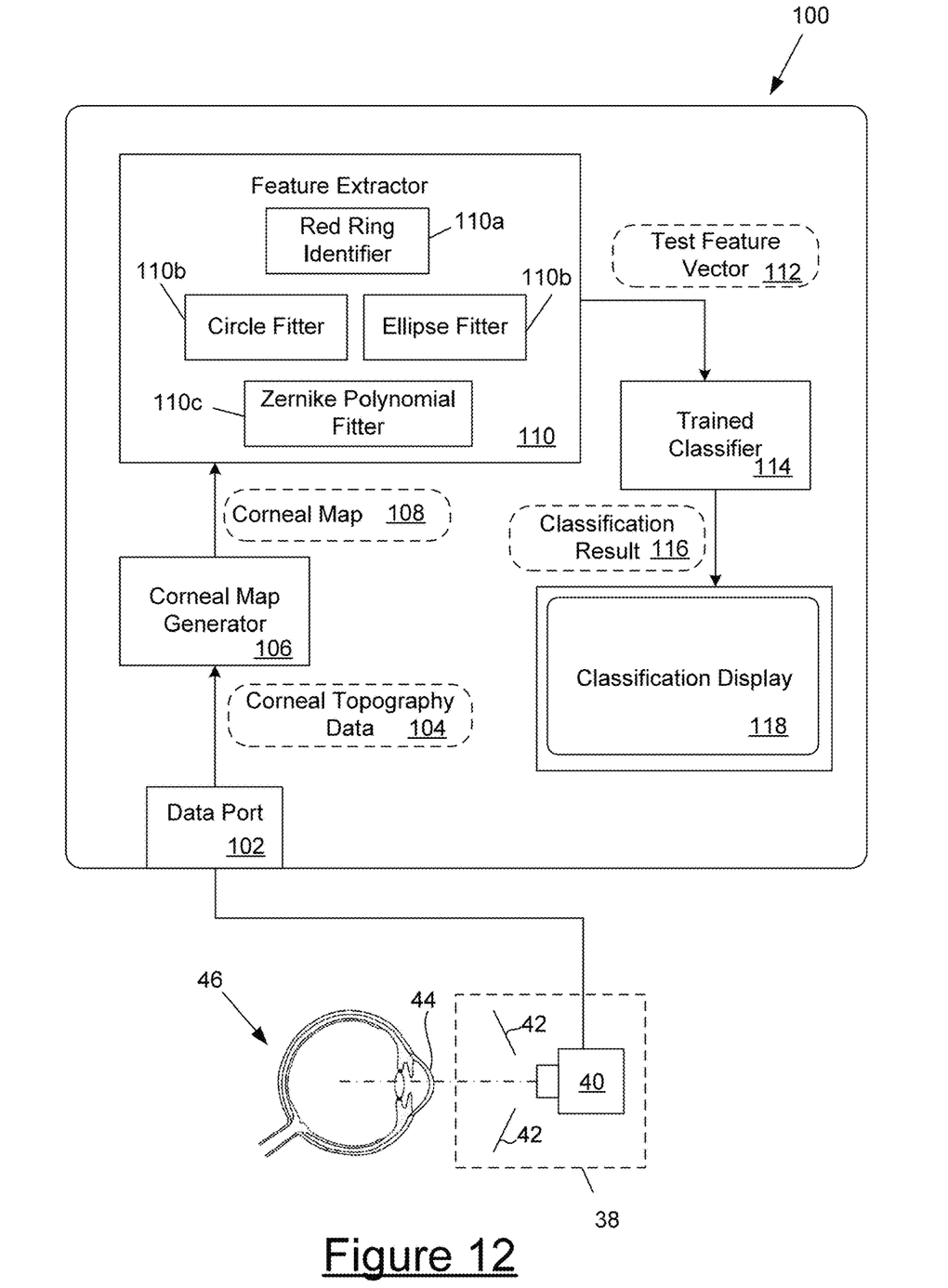
FIG. 12 depicts a dedicated apparatus for classifying corneal topography maps into one of a number of classes

FIG. 12, depicts a dedicated apparatus 100 for classifying corneal topography maps into one of a number of classes. Apparatus 100 may be implemented using dedicated circuitry or as a suitably programmed computer such as that illustrated in FIG. 1. The apparatus 100 includes a data port 102 for coupling to the output of a corneal topographer 38. Corneal topography electronic data 104 proceeds from the data port 102 in use. An input unit in the form of a corneal map generator 106 is provided that is arranged to convert the corneal topography data 104 from the corneal topographer 38, into a corneal map 108, that comprises a file or stream of data packets which are transmitted along electronic conductors of the apparatus 100.

A feature extractor unit 110 (the term unit is used equivalently to "assembly" or "component") is provided that is responsive to the corneal map generator 106 and which is arranged to process the corneal map 108 to produce a corresponding test feature vector 112. The feature extraction unit 110 includes a number of sub-assemblies being a red ring identifier 110a to identify a red ring of the map 108 and also a circle fitter 110b and an ellipse fitter 110c to fit one or more shapes to the red ring, i.e. a circle and an ellipse, wherein parameters of said shapes comprise features of the feature vector 112. The Feature extractor unit 110 also includes a Zernike polynomial fitter sub-assembly 110d that is arranged to process the corneal map 108 to fit Zernike polynomials thereto. Weights of the fitted Zernike polynomials comprise further features of the test feature vector 112.

Apparatus 100 includes a trained classification unit 114 that is provided in communication with an output side of the feature extraction unit 110. Classification unit 114 is trained to classify test vectors, e.g. test feature vector 112 for corneal maps as one of at least:
I. "bullseye" OR "central island", and
II. "smiley face", and
III. "frowney face", and
IV. "lateral decentration"; and The classification unit 114 generates a classification result signal 116. The apparatus 100 includes an electronic display 118 that is responsive to the classification unit for presenting classifications to a human user. For example the human user may be a health professional that can then use the classification to apply suitable therapy to the patient, including fitting an OK lens for example.

Embodiments of the invention make use of Zernike polynomials to reduce the number of features describing corneal topography axial curvature difference maps to allow more efficient and accurate machine learning classification.

Furthermore, a method has been provided to automatically calculate the centre coordinates and dimensions of the red ring observed in corneal topography tangent curvature difference maps.

In one embodiment a method is provided to fit Zernike polynomial values and red ring classification data to form a training set that can be used to train a machine learning algorithm including, but not limited to Decision Forest; Decision Jungle; Logistic Regression, Neural Networks and Support Vector Machines for reliable classification of post orthokeratology contact lens wear fit characteristics from corneal topography difference maps.

The Inventor has found that the above methods when used in a Multiclass Decision Forest, Support Vector Machine or Neural Network algorithm provide at least 80% accuracy of classification of post orthokeratology wear corneal topography difference maps with as little as 1000 training examples.

The Inventor has observed that, in a preferred embodiment, reducing the number of features to:
- 14 Zernike components from axial curvature difference map data measured over a 3.5 mm pupil,
- 14 Zernike components from axial curvature and tangential curvature difference map data measured over a 5.5 mm pupil,
- the XY coordinates of a least squares fit circle to superimpose the red (positive power, least curvature) ring observed in tangential curvature difference map data; and
- the long and short axes of the best fit ellipse to coincide with the red ring, to form 32 features, retains sufficient information to provide at least 80% accuracy of post orthokeratology wear corneal topography difference maps.

Although the method for establishing the influential components of the red ring fit is best applied to tangential curvature corneal topography difference maps representing orthokeratology lens wear, the same process can be applied to any type of corneal topography difference map data including but not limited to axial curvature, axial dioptric power, tangential curvature, tangential dioptric power, refractive power, elevation relative to a best fit sphere and corneal sagittal height.

Although the method for establishing Zernike fit components is best applied to axial curvature and tangential corneal topography difference maps representing orthokeratology lens wear, the same process can be applied to any type of corneal topography difference map data including but not limited to axial curvature, axial dioptric power, tangential curvature, tangential dioptric power, refractive power, elevation relative to a best fit sphere and corneal sagittal height.

The Inventor has found that Zernike components Z4 (defocus), Z7 (vertical coma), Z8 (horizontal coma), Z12 (spherical aberration), Z17 (vertical secondary coma), Z18 (horizontal secondary coma), and Z24 (secondary spherical aberration) fitted to 3.5 mm and 5.5 mm pupil diameters are the most informative Zernike features for post orthokeratology wear corneal topography difference map classification using machine learning, but that other Zernike polynomial terms could instead be used over other pupil diameters that do exceed the dimensions of the available data.

Embodiments of the invention are not limited to Zernike polynomial fitting and can be similarly used but not limited to other types of mathematical modelling of 3-dimensional shapes such as Fourier Analysis and United Movement Invariants, Principal Component Analysis and variations of Zernike polynomial shape fitting.

In one embodiment the procedures for classification machine training and classification can be hosted in a cloud based setting to allow upload of raw corneal topography maps used in orthokeratology lens fitting, where they can be process using the processes outlined above to return a classification and probability score describing the accuracy of the classification.

In compliance with the statute, the invention has been described in language more or less specific to structural or methodical features. The term "comprises" and its variations, such as "comprising" and "comprised of" is used throughout in an inclusive sense and not to the exclusion of any additional features.

It is to be understood that the invention is not limited to specific features shown or described since the means herein described comprises preferred forms of putting the invention into effect.

The invention is, therefore, claimed in any of its forms or modifications within the proper scope of the appended claims appropriately interpreted by those skilled in the art.

Throughout the specification and claims (if present), unless the context requires otherwise, the term "substantially" or "about" will be understood to not be limited to the value for the range qualified by the terms.

Any embodiment of the invention is meant to be illustrative only and is not meant to be limiting to the invention. Therefore, it should be appreciated that various other changes and modifications can be made to any embodiment described without departing from the spirit and scope of the invention.

The invention claimed is:

1. A method to therapeutically treat an eye condition related to the shape of the cornea, the method comprising the steps of:
    applying a corneal topography apparatus to a patient to capture a map of a cornea of the patient in a computer;
    extracting one or more feature vectors from the map including at least features identifying a red ring of the cornea;
    applying the one or more feature vectors to a classification machine trained to classify the map as one of at least:
        i. "bullseye" OR "central island", and
        ii. "smiley face", and
        iii. "frowney face", and
        iv. "lateral decentration"; and
    subsequently treating the patient taking into account a classification produced by the classification machine.

2. The method of claim 1, wherein the step of extracting the features identifying the red ring of the cornea include determining center coordinates of a circle fitted to a red ring observed in the map.

3. The method according of claim 1, wherein the step of extracting the features identifying the red ring of the cornea includes determining long and short axes of an ellipse fitted to the red ring.

4. The method of the claim 1, wherein the map comprises a difference map, wherein the method includes the steps of:
    applying the corneal topography apparatus to the patient to capture a baseline map of a cornea of the patient in the computer;
    subsequent to the patient wearing an OK lens on the cornea applying the corneal topography apparatus to the patient to capture a post-wear map of the cornea in the computer; and
    deriving the difference map from the baseline map and the post-wear map.

5. The method of claim 4, wherein the step of subsequently treating the patient taking into account the classification produced by the classification machine, includes fitting an OK lens to the patient wherein said lens is selected based on the classification of the classification machine of the difference map.

6. The method of claim 1, wherein the step of extracting one or more feature vectors from the map includes extracting curvature estimates of the map and applying the one or more features to a classification machine trained to classify the map as one of at least:
    i. "bullseye", and
    ii. "smiley face", and
    iii. "frowney face", and
    iv. "lateral decentration", and
    v. "central island".

7. The method of claim 6, including extracting the curvature estimates of the difference map by fitting Zernike polynomials thereto.

8. The method of claim 7, including fitting Z4, Z7, Z8, Z12, Z17, Z18 and Z24 Zernike polynomials.

9. The method of claim 7, including obtaining features corresponding to 14 Zernike components from axial curvature map data measured over a 3.5 mm pupil.

10. The method of claim 9, including obtaining features corresponding to the 14 Zernike components from the axial curvature and tangential curvature difference maps data measured over a 5.5 mm pupil.

11. The method of claim 1, wherein the classification machine includes one of:
    a Decision Forest; Decision Jungle; Logistic Regression Machine; Neural Network;
    Support Vector Machine.

12. An apparatus for classifying corneal topography maps into one of a number of classes including:
    an input unit arranged to convert data generated by a corneal topographer into a corneal map;
    a feature extraction unit responsive to the input unit and arranged to process the corneal map to produce a corresponding test feature vector, wherein the feature extraction unit is arranged to identify a red ring of the corneal map and to fit one or more shapes to the red ring wherein parameters of said one or more shapes comprise features of the feature vector;

a classification unit trained to classify test vectors for corneal maps and responsive to the feature extraction unit, wherein the classification unit is arranged to classify the test feature vector as one of at least:
  I. "bullseye" OR "central island", and
  II. "smiley face", and
  III. "frowney face", and
  IV. "lateral decentration"; and an electronic display that is responsive to the classification unit for presenting classifications to a human user.

13. The apparatus of claim 12, wherein the feature extraction unit is arranged to fit shapes comprising a circle and an ellipse to the red ring.

14. The apparatus of claim 13, wherein the feature extraction unit is arranged to process the corneal map to fit Zernike polynomials thereto to derive fitted polynomials,
  wherein weights of said fitted polynomials comprise further features of the test feature vector and
  wherein the classification unit is trained to classify test vectors including said weights to classify the test feature vector as one of at least:
    i. "bullseye", and
    ii. "smiley face", and
    iii. "frowney face", and
    iv. "lateral decentration", and
    v. "central island".

15. A method for fitting OK lenses to a patient comprising the steps of:
  applying a corneal topography apparatus to a patient to capture a baseline and post wear maps of a cornea of the patient in a computer to thereby derive a difference map;
  processing the difference map to fit Zernike polynomials thereto to derive fitted polynomials, wherein weights of said fitted polynomials comprise features of a test feature vector for the difference map;
  applying the test feature vector to a classification machine trained to classify the difference map as one of a number of classes; and
  subsequently treating the patient taking into account the classification machine's classification.

16. The apparatus of claim 12 implemented by means of a cloud server platform.

17. An apparatus for classifying corneal topography maps into one of a number of predetermined classes, the apparatus including:
  an input unit for converting data from a corneal topography unit into a corneal map;
  a feature extraction unit arranged to process the corneal map to fit Zernike polynomials thereto to derive fitted polynomials, wherein weights of said fitted polynomials comprise further features of a test feature vector;
  a classification unit trained to classify test vectors for corneal maps and responsive to the feature extraction unit,
  wherein the classification unit is arranged to classify the test feature vector as corresponding to one of a number of predetermined classes"; and
  an electronic display that is responsive to the classification unit for presenting classifications to a human user.

18. The apparatus of claim 17 in combination with the corneal topography unit.

19. A method to therapeutically treat an eye condition related to the shape of the cornea, the method comprising the steps of:
  applying a corneal topography apparatus to a patient to capture a corneal map of a cornea of the patient in a computer;
  processing the corneal map to fit Zernike polynomials thereto to derive fitted polynomials, wherein weights of said fitted polynomials comprise features of a test feature vector;
  applying the test feature vector to a classification machine trained to classify a difference map as one of a number of predetermined classes; and
  subsequently treating the patient taking into account a classification of the classification machine.

* * * * *